United States Patent
Barrow et al.

(10) Patent No.: US 7,361,363 B2
(45) Date of Patent: Apr. 22, 2008

(54) SILKY FEEL COSMETIC EMULSION CHASSIS BASED ON GLYCERIN AND CHEMICALLY MODIFIED STARCH

(75) Inventors: Stephen Roy Barrow, Trumbull, CT (US); Michael Charles Cheney, Trumbull, CT (US); Brian John Dobkowski, Milford, CT (US); Christy Ann Bridges, Fairfield, CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 711 days.

(21) Appl. No.: 10/697,608

(22) Filed: Oct. 30, 2003

(65) Prior Publication Data

US 2004/0241128 A1 Dec. 2, 2004

(51) Int. Cl.
*A61K 8/02* (2006.01)
*A61K 8/73* (2006.01)

(52) U.S. Cl. ................... 424/401; 424/70.13; 514/778; 514/844

(58) Field of Classification Search ................ 424/401, 424/70.13, 62; 514/778, 844
See application file for complete search history.

(56) References Cited

U.S. PATENT DOCUMENTS

| | | | |
|---|---|---|---|
| 4,894,222 A | 1/1990 | Matravers | |
| 5,215,759 A * | 6/1993 | Mausner | ..................... 424/489 |
| 5,256,404 A | 10/1993 | Martino et al. | |
| 5,453,281 A * | 9/1995 | Whistler | ..................... 424/465 |
| 6,248,338 B1 | 6/2001 | Muller et al. | |
| 6,294,182 B1 | 9/2001 | Znaiden et al. | |
| 6,322,799 B1 | 11/2001 | Ilardi et al. | |
| 6,342,470 B1 | 1/2002 | Aronson | |
| 2001/0055574 A1* | 12/2001 | Franklin et al. | .............. 424/65 |
| 2002/0131946 A1 | 9/2002 | Pham et al. | |
| 2003/0206931 A1* | 11/2003 | Moghe et al. | .............. 424/401 |

FOREIGN PATENT DOCUMENTS

| | | |
|---|---|---|
| WO | 01/54663 | 8/2001 |
| WO | 01/70270 | 9/2001 |

OTHER PUBLICATIONS

Lubriderm Skin Renewal Age Defying Hand Cream—copy of carton.
Lubriderm Skin Renewal Firming Body Lotion—copy of carton.
Technical Bulletin—Pure-Gel® Starches for Personal Care Applications.

* cited by examiner

*Primary Examiner*—Sreeni Padmanabhan
*Assistant Examiner*—Umamaheswari Ramachandran
(74) *Attorney, Agent, or Firm*—Milton L. Honig

(57) ABSTRACT

A cosmetic composition is provided which includes a high level of glycerin, a chemically modified starch which is preferably a hydroxypropyl di-starch phosphate or an acetylated di-starch adipate, and a crystalline gel structurant comprising a surfactant and co-surfactant, the structurant having an enthalpy ranging from about 2 to about 15 Joule per gram. The composition has a silky sensory feel and exhibits a positive normal force, preferably ranging from about +0.5 to about +5 grams. The glycerin to chemically modified starch is present in a weight ratio ranging from about 100:1 to about 2:1. Advantageously, the composition has a SkiCon Value ranging from about 10 to about 80.

11 Claims, No Drawings

SILKY FEEL COSMETIC EMULSION CHASSIS BASED ON GLYCERIN AND CHEMICALLY MODIFIED STARCH

BACKGROUND OF THE INVENTION

1. Field of the Invention

The invention concerns a cosmetic emulsion base with silky feel aesthetics.

2. The Related Art

Aesthetics are an important attribute of a cosmetic lotion or cream. Consumers' judgement of such products is significantly determined by the aesthetics of skinfeel.

Similar to different models of an automobile, cosmetic products often use a common chassis as a base formulation. Product line variants such as moisturizing, anti-aging, herbal and sunscreen formulations usually dose the featured variant additive at levels of less than 5% into a concentrated chassis. Manufacture costs are reduced through use of a chassis system.

The difficulty has been to devise a chassis with the appropriate skinfeel aesthetics. Furthermore, it is desirable to include high levels of glycerin for moisturization. This presents a challenge for thickening and emulsifying agents to overcome the negative feel of glycerin.

U.S. 2002/0131946 A1 (Pham et al.) discloses non-sticky cosmetic moisturizing compositions based on glycerin and polymeric wetting agents one of which is described as Pemulen® TR2. Other than removing stickiness, there is no disclosure that these compositions impart any particular skinfeel advantage.

There is a need for a cosmetic concentrate chassis which delivers a silky skinfeel which can be formulated with a variety of actives and promotional ingredients. Still another need is to provide a concentrate with exceptional aesthetics and that imparts a high level of moisturization when applied to the body.

SUMMARY OF THE INVENTION

A cosmetic composition is provided which includes:
(i) a moisturizing effective amount of glycerin;
(ii) a sensory effective amount of a modified starch selected from the group consisting of a $C_2$-$C_5$ hydroxyalkyl starch and a $C_2$-$C_{18}$ acyl starch;
(iii) from about 1 to about 30% of a crystalline gel structurant comprising a surfactant and co-surfactant in an amount and type exhibiting an enthalpy as measured by Differential Scanning Calorimetry ranging from about 2 to about 15 Joule per gram, and wherein the composition has a normal force of from about +0.5 to about +5 grams thereby achieving a silky sensory feel on skin, the glycerin to modified starch being present in a weight ratio ranging from about 100:1 to about 2:1.

DETAILED DESCRIPTION OF THE INVENTION

Cosmetic compositions of the present invention are provided with a moisturization effective amount of glycerin which also is known as glycerol in the art. Amounts of glycerin may range from about 5% to about 50%, preferably from 10% to 40%, more preferably from 12 to 35%, optimally from 15 to 30% by weight of the composition.

Another component of compositions according to the present invention is that of a chemically modified starch. In one embodiment, the starch is $C_2$-$C_5$ hydroxyalkyl starch. It is assumed that the formation of a hydroxyl group, which is bound to the starch backbone via an alkyl group with 2 to 5 carbon atoms, leads to a suitable hydrophilic-lipophilic balance of the starch. The position of the hydroxyl group on the alkyl group is not critical and can be in the alpha to omega position. The degree of substitution of the hydroxyalkylation is preferably approximately 0.08 to 0.3. The degree of substitution is the average number of substituted OH groups of the starch molecule per anhydroglucose unit. The hydroxyalkylation of a native starch can be brought about by reacting a native starch with alkylene oxides with the appropriate number of carbon atoms. Particularly preferred are hydroxyethylated and/or hydroxypropylated starches obtained by reacting starches with ethylene oxide or propylene oxide. A starch to be used according to the invention can also contain more than one hydroxyl group per alkyl group.

In another embodiment the starch is a $C_2$-$C_{18}$ acyl starch. This starch regularly occurs if crosslinking has been brought about by $C_2$-$C_{18}$ alkanoate or alkenoate and can be additionally acylated with a view to a suitable hydrophilic-lipophilic balance with a degree of substitution of 0 to 0.8, particularly 0 to 0.5. Acylation generally takes place by reaction with acid anhydrides of general formula (R—C(O))$_2$O, in which R is an alkyl group, such as methyl or ethyl, with succinic or maleic anhydride or their alkylated derivatives.

A particularly preferred starch derivative for purposes of the invention is a hydroxypropyl di-starch phosphate, as well as acetylated di-starch adipate.

Most preferred is sodium hydroxypropyl starch phosphate available from the National Starch and Chemical Company and from Grain Processing Corporation, the latter under the trademark Pure-Gel®.

The chemically modified starches of the present invention normally are crosslinked. A preferred crosslinking method is phosphorylation, in which the starch is reacted with phosphorous oxychloride, phosphorous pentoxide, and/or sodium trimetaphosphate. Two starch chains are crosslinked by an anionic P—O group. A further preferred crosslinking method is by using a $C_4$-$C_{18}$ alkane or alkene dicarboxylic acids, preferably $C_4$-$C_8$ alkane dicarboxylic acids, and in particular adipic acid. The alkane or alkene dicarboxylic acid links two starch chains via ester bonds. It can be in straight or branched chain form. The derivatives are obtained, e.g., by reacting starch with the mixed anhydrides of dicarboxylic acid and acetic acid. Based on the dry starch, in general less than 0.1 wt. %, normally about 0.06 wt. %, crosslinking agent is used.

Chemically modified starches may either be non-gelatinized or pre-gelatinized, with the former preferred. Amounts of the chemically modified starch may range from about 0.1 to about 20%, preferably from about 0.5 to about 10%, optimally from about 1 to about 5% by weight of the composition.

Relative amounts by weight of glycerin to the chemically modified starch may range from about 100:1 to about 2:1, preferably from about 50:1 to about 5:1; optimally from about 15:1 to about 8:1.

A crystalline gel structurant will also be present in compositions according to the present invention. The structurant will include both a surfactant and a co-surfactant. Preferred surfactants are $C_1$-$C_{200}$ esters of $C_{10}$-$C_{22}$ fatty acid. Esters of the fatty acid preferably are polyol esters such as $C_2$-$C_3$ alkoxylated alcohol esters. Among these are the polyethoxy, polypropoxy and block polyethyoxy/polypropoxy alcohol esters.

Particularly preferred are such esters as PEG-100 stearate, PEG-20 stearate, PEG-80 laurate, PEG-20 laurate, PEG-100 palmitate, PEG-20 palmitate and combinations thereof.

The co-surfactant typically may be a combination of a $C_{10}$-$C_{22}$ fatty alcohol, glyceryl esters of a $C_{10}$-$C_{22}$ fatty acid, and a $C_{10}$-$C_{22}$ unesterified fatty acid. Relative amounts of the ester to the alcohol may range from about 100:1 to about 1:100, preferably from about 50:1 to about 1:50, and optimally from about 3:1 to about 1:3 by weight. Relative amounts of the combination of glyceryl ester and fatty alcohol to unesterified fatty acid may range from about 100:1 to about 1:100, preferably from about 50:1 to about 1:50, and optimally from about 3:1 to about 1:3 by weight. Typical fatty alcohols include behenyl alcohol, stearyl alcohol, cetyl alcohol, myristyl alcohol, lauryl alcohol, oleyl alcohol and combinations thereof.

The relative amount of surfactant and co-surfactant may range from about 50:1 to about 1:50, preferably from about 10:1 to about 1:10, and optimally from about 3:1 to about 1:3 by weight.

A crystalline gel structurant is formed by the surfactant and co-surfactant. Indeed, the surfactant and co-surfactant combination in their relative ratio and type of material is defined by an enthalpy which may range from about 2 to about 15, preferably from about 2.5 to about 12, and optimally from about 3.5 to about 8 Joules per gram, as measured by Differential Scanning Calorimetry. Furthermore, the crystalline gel structurant system advantageously may have a melting point ranging from about 30 to about 70° C., preferably from about 45 to about 65° C., and optimally from about 50 to about 60° C.

Compositions of the present invention are not limited by any pH range. However, a preferred pH ranges from about 5.5 to about 8.

Thickeners other than the chemically modified starch may but are ordinarily not necessary in compositions according to this invention. By the term thickener is meant any material which at 2% in water generates a viscosity greater than 5,000 cps, particularly greater than 10,000 cps as measured on a Brookfield RVT model viscometer at spindle speed of 20 rpm in a pH range 7.2 to 7.6.

Normal forces which are positive numbers reflect a silky smooth skinfeel of the formulation. Negative values have been identified with a draggy feel which many consumers dislike. Normal force is measured in the following manner. A rheometer that has a shear rate mode capability and a normal force transducer is utilized to measure the high shear normal force. These devices are available from Rheometric Scientific ARES, TA Instruments AR2000, and Paar Physica MCR. Samples are compressed between concentric parallel plates of diameter 25 mm and gap (vertical distance between the two plates) of 100 microns. The measurements are made in a continuous logarithmic shear sweep mode with a shear rate range of 0.1 to 10,000 $s^{-1}$. Each sweep takes 5 minutes and is conducted at ambient condition (20-25° C.). The normal force is calculated by subtracting the baseline (defined as the normal force value at or near 100 $s^{-1}$) from the highest normal force value measured between 1000 and 10,000 $s^{-1}$. A positive normal force of about 0.5 grams and especially about 1 gram or greater is correlated to products/ materials with silky sensations during rubbing in application.

The higher the positive value of the normal shear force the better are the aesthetics. Ordinarily, excellent aesthetics are achieved when the normal shear force ranges from about +0.5 to about +5 grams. Particularly desirable is a positive shear force in the range from about +1 to about +2.5 grams.

Moisturization is an important aspect along with the sensory feel of compositions of this invention. For this reason, the compositions may advantageously have a SkiCon Value ranging from about 10 to about 80, preferably from about 20 to about 70, optimally from about 25 to about 60.

The SkiCon Value is measured with a SkiCon 200 instrument. Moisturization is measured on the skin surface through a conductance evaluation (micro Siemens). Depth of measurement is approximately less than 15 µm. The methodology involves use of panelists (usually 10-20 in number). These panelists are requested to pre-wash with a standard Ivory® soap. After 30 minutes, the panelists' skin are measured using the SkiCon 200 instrument. A sample of 0.05 gram experimental product is then applied onto a 5×5 cm area marked on an inner forearm. Post-application measurements are taken two hours after the initial treatment.

Advantageously, compositions of the present invention will have low foamability. Lather Volume as measured by the Lather Volume Test described in U.S. Pat. No. 6,153,208, herein incorporated by reference, ordinarily will be less than 60 ml but preferably less than 30 ml.

A variety of other components may be present in the concentrates of the present invention. Foremost is that of water. Amounts of water may range from about 1 to about 90%, preferably from about 30 to about 80%, optimally from about 50 to about 80% by weight.

Emollient materials may be included in compositions of this invention. These may be in the form of silicone oils, synthetic esters and hydrocarbons. Amounts of the emollients may range anywhere from about 0.1 to about 95%, preferably between about 1 and about 50% by weight.

Silicone oils may be divided into the volatile and nonvolatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5\times10^{-6}$ to 0.1 $m^2/s$ at 25° C. Among the preferred nonvolatile emollients useful in the present compositions are the polydimethyl siloxanes having viscosities from about $1\times10^{-5}$ to about $4\times10^{-4}$ $m^2/s$ at 25° C.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Among the ester emollients are:
(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.

(4) Wax esters such as beeswax, spermaceti wax and tribehenin wax.

(5) Sterols esters, of which cholesterol fatty acid esters are examples thereof.

(6) Sugar ester of fatty acids such as sucrose polybehenate and sucrose polycottonseedate.

Hydrocarbons are suitable further ingredients. These include petrolatum, mineral oil, $C_{11}$-$C_{13}$ isoparaffins, polyalphaolefins, and especially isohexadecane, available commercially as Permethyl 101A from Presperse Inc.

Humectants of the polyhydric alcohol-type in addition to glycerin can be employed with formulations of this invention. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from 0.5 to 50%, preferably between 1 and 15% by weight of the composition.

Sunscreen actives may also be included in compositions of the present invention. Particularly preferred are such materials as ethylhexyl p-methoxycinnamate, available as Parsol MCX®, Avobenzene, available as Parsol 1789® and benzophenone-3, also known as Oxybenzone. Inorganic sunscreen actives may be employed such as microfine titanium dioxide, zinc oxide, polyethylene and various other polymers. Amounts of the sunscreen agents when present may generally range from 0.1 to 30%, preferably from 2 to 20%, optimally from 4 to 100% by weight.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Compositions of the present invention may also contain vitamins. Illustrative water-soluble vitamins are Niacinamide, Vitamin $B_2$, Vitamin $B_6$, Vitamin C and Biotin. Among the useful water-insoluble vitamins are Vitamin A (retinol), Vitamin A Palmitate, Ascorbyl Tetraisopalmitate, Vitamin E (tocopherol), Vitamin E Acetate and DL-panthenol. Total amount of vitamins when present in compositions according to the present invention may range from 0.001 to 10%, preferably from 0.01% to 1%, optimally from 0.1 to 0.5% by weight.

Another adjunct ingredient can be that of an enzyme. Particularly preferred is superoxide dismutase, commercially available as Biocell SOD from the Brooks Company, USA.

Skin lightening agents may be included in the compositions of the invention. Illustrative substances are placental extract, lactic acid, niacinamide, arbutin, kojic acid, resorcinol and derivatives including 4-substituted resorcinols and combinations thereof. Amounts of these agents may range from about 0.1 to about 10%, preferably from about 0.5 to about 2% by weight of the compositions.

Desquamation agents are further optional components. Illustrative are the alpha-hydroxycarboxylic acids and beta-hydroxycarboxylic acids. Among the former are salts of glycolic acid, lactic acid and malic acid. Salicylic acid is representative of the beta-hydroxycarboxylic acids. Amounts of these materials when present may range from about 0.1 to about 15% by weight of the composition.

A variety of herbal extracts may optionally be included in compositions of this invention. Illustrative are green tea, chamomile, licorice and extract combinations thereof. The extracts may either be water soluble or water-insoluble carried in a solvent which respectively is hydrophilic or hydrophobic. Water and ethanol are the preferred extract solvents.

Anti-microbial agents may also be included in the compositions of this invention. Illustrative are trichlosan, trichlocarban, Octopyrox® and zinc pyrithione. Amounts may range from about 0.01 to about 5%, preferably from about 0.1 to about 0.5% by weight of the composition.

Colorants, fragrances, opacifiers and abrasives may also be included in compositions of the present invention. Each of these substances may range from about 0.05 to about 5%, preferably between 0.1 and 3% by weight.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

EXAMPLE 1

A series of high level glycerin formulations were evaluated as concentrate chassis to understand their skinfeel properties reflected in their normal force profile. These experiments focused upon the surfactant/co-surfactant ratio and effect of PureGel® in the presence of glycerin. The test formulations are outlined in Table I below.

The surfactant in these formulations is PEG-100 Stearate. Co-surfactant is the combination of stearic acid, glycerol monostearate/stearamide AMP, glycerol monostearate and cetyl alcohol.

TABLE I

| | Sample (Weight %) | | |
|---|---|---|---|
| Components | 1 | 2 | 3 |
| Oil Phase | | | |
| Stearic Acid | 2.669 | 2.371 | 0.290 |
| Glycerol Monostearate/Stearamide AMP | 1.576 | 1.401 | 0.180 |
| Glycerol Monostearate | 0.735 | 0.654 | 0.080 |
| Cetyl Alcohol | 0.420 | 0.374 | 0.050 |
| PEG-100 Stearate | 0.600 | 1.200 | 5.400 |
| Aqueous Phase | | | |
| Water | 73.860 | 73.860 | 73.860 |
| Disodium EDTA | 0.050 | 0.050 | 0.050 |
| Glycerin | 18.000 | 18.000 | 18.000 |
| Sodium Hydroxypropyl Starch Phosphate | 2.000 | 2.000 | 2.000 |
| Glydant Plus ® | 0.090 | 0.090 | 0.090 |

The formulations were evaluated for their normal force values at high shear. Table II outlines the results of that evaluation.

TABLE II

| Sample | Surfactant/Co-Surfactant | Normal Force (gm) |
|---|---|---|
| 1 | 10/90 | 0.27 |
| 2 | 20/80 | 2.54 |
| 3 | 90/10 | −4.75 |

Evident from Table II is that a silky skinfeel in the presence of a high level of glycerol is reflected by a positive normal force value. The positive normal force is attained through the use of sodium hydroxypropyl starch phosphate (PureGel®). Particularly good performance is found where the surfactant/co-surfactant ratio is 20:80. The operative range by extrapolation lies between about 15:85 and 60:40.

EXAMPLE 2

This Example illustrates the enthalpy values associated with the crystalline gel structurant according to the present invention. The formulas evaluated are the ones listed in Table III below.

TABLE III

| | Sample (Weight %) | | |
|---|---|---|---|
| Components | 1 | 2 | 3 |
| Oil Phase | | | |
| Stearic Acid | 2.075 | 2.371 | 2.669 |
| Glycerol Monostearate/Stearamide AMP | 1.226 | 1.401 | 1.576 |
| Glycerol Monostearate | 0.572 | 0.654 | 0.735 |
| Cetyl Alcohol | 0.327 | 0.374 | 0.420 |
| PEG-100 Stearate | 1.80 | 1.200 | 0.600 |
| Aqueous Phase | | | |
| Water | 75.860 | 75.860 | 75.860 |
| Disodium EDTA | 0.050 | 0.050 | 0.050 |
| Glycerin | 18.000 | 18.000 | 18.000 |
| Glydant Plus ® | 0.090 | 0.090 | 0.090 |

Enthalpy values for the structurant/co-structurant systems in Table IV are listed in Table IV below

TABLE IV

| Nonionic Crystalline Gel Structurant | | | |
|---|---|---|---|
| Sample | Surfactant:Co-Surfactant | Melting Point (° C.) | Melting/Heating Ethalpy (J/g) |
| 1 | 30:70 | 52.98 | 7.26 |
| 2 | 20:80 | 51.73 | 6.17 |
| 3 | 10:90 | 51.14 | 10.77 |

EXAMPLE 3

A formulation typical of the present invention is outlined below.

TABLE V

| Ingredients | Weight % |
|---|---|
| Water | |
| Water | Balance |
| Surfactant Network | |
| Stearic Acid | 2.3720 |
| Glycerol Monostearate/Stearamide AMP | 1.4008 |
| Glycerol Monostearate | 0.6537 |
| Cetyl Alcohol | 0.3735 |
| PEG-100 Stearate | 1.2000 |
| Humectant/Emollient | |
| Petrolatum | 0.2500 |
| Glycerin | 18.0000 |
| Caprylic/Capric Triglyceride | 4.2500 |
| Silicone | |
| Silicone Fluid 200/50 cts | 2.0000 |
| Cyclomethicone (DC 345) | 1.0000 |
| Polymers | |
| PureGel B994 ® | 2.5000 |
| Preservatives/Color | |
| Disodium EDTA | 0.0500 |
| Methylparaben | 0.1425 |
| Titanium Dioxide | 0.1000 |
| DMDM Hydantoin | 0.2500 |
| Fragrance | |
| Fragrance | 0.2500 |

The normal force value of the composition outlined in Table V was 0.56 gram.

What is claimed is:
1. A cosmetic composition comprising:
(i) from about 10 to about 50% of glycerin;
(ii) a sensory effective amount of a non-gelatinized modified starch selected from the group consisting of a $C_2$-$C_5$ hydroxyalkyl starch and a $C_2$-$C_{18}$ acyl starch;

(iii) from about 1 to about 30% of a crystalline gel structurant comprising a surfactant and co-surfactant in an amount and type exhibiting an enthalpy as measured by Differential Scanning Calorimetry ranging from about 2 to about 15 Joule per gram, and wherein the composition has a normal force of from about +0.5 to about +5 grams thereby achieving a silky sensory feel on skin, the glycerin to modified starch being present in a weight ratio ranging from about 100:1 to about 2:1, the surfactant being a polyethoxy or polypropoxy alcohol ester of a fatty acid and the co-surfactant being a mixture of $C_{10}$-$C_{22}$ fatty alcohol, a glyceryl ester of $C_{10}$-$C_{22}$ fatty acid and stearic acid, the surfactant and co-surfactant being present in a range between about 15:85 and 60:40.

2. The composition according to claim 1 wherein the chemically modified starch is a hydroxypropyl di-starch phosphate or an acetylated di-starch adipate.

3. The composition according to claim 1 wherein glycerin is present from about 12 to about 35% by weight.

4. The composition according to claim 1 having a SkiCon Value ranging from about 10 to about 80.

5. The composition according to claim 1 wherein the crystalline gel structurant has a melting point ranging from about 30 to about 70° C.

6. The composition according to claim 1 wherein the surfactant and co-surfactant are present by weight ratio from about 50:1 to about 1:50.

7. The composition according to claim 6 wherein the glycerol ester and fatty alcohol are present by weight ratio from about 100:1 to about 1:100, and a combination of glyceryl ester and fatty alcohol with respect to stearic acid are present by weight ratio from about 100:1 to about 1:100.

8. The composition according to claim 1 wherein the glyceryl ester and fatty alcohol are present by weight ratio from about 3:1 to about 1:3, and a combination of glyceryl ester and fatty alcohol with respect to stearic acid are present by weight ratio from about 3:1 to about 1:3.

9. The composition according to claim 1 wherein the polyethoxy or polypropoxy alcohol ester of a fatty acid is PEG-100 stearate.

10. The composition according to claim 1 wherein the surfactant and co-surfactant are present by weight ratio from about 3:1 to about 1:3.

11. The composition according to claim 1 wherein the surfactant and co-surfactant are present at about 20:80 relative weight ratio.

* * * * *